(12) United States Patent
Takaki et al.

(10) Patent No.: US 7,556,962 B2
(45) Date of Patent: Jul. 7, 2009

(54) SACCHARIDE COMPOSITION PURIFICATION INSTRUMENT

(75) Inventors: Masanori Takaki, Hitachinaka (JP);
Kuriko Yamada, Sapporo (JP);
Kisaburo Deguchi, Sapporo (JP);
Hiroaki Nakagawa, Sapporo (JP);
Shinichiro Nishimura, Sapporo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 588 days.

(21) Appl. No.: 11/061,536

(22) Filed: Feb. 18, 2005

(65) Prior Publication Data
US 2006/0121559 A1    Jun. 8, 2006

(30) Foreign Application Priority Data
Mar. 31, 2004   (JP)   ............... 2004-101799

(51) Int. Cl.
*C12M 1/14*   (2006.01)
*C12M 3/04*   (2006.01)

(52) U.S. Cl. ................ 435/299.1; 435/68.1; 435/287.1; 210/656

(58) Field of Classification Search ................ 435/68.1, 435/287.1, 299.1; 210/656
See application file for complete search history.

(56) References Cited

U.S. PATENT DOCUMENTS 4,013,511 A  *  3/1977  Goldstein et al. .......... 435/181
4,191,810 A  *  3/1980  Yoshikazu et al. .......... 435/177
4,217,415 A  *  8/1980  Barabino et al. .............. 435/98
2001/0051675 A1 * 12/2001 Ichikawa et al. .............. 524/18

FOREIGN PATENT DOCUMENTS

WO    WO 03/004597    *   1/2003

OTHER PUBLICATIONS

"Demonstration of a New Amidase Acting on Glycopeptides" by Noriko Takahashi, Biochemical and Biophysical Research Communications, vol. 76, Nov. 4, 1977, pp. 1194- Copyright 1997 by Academic Press, Inc.

"Demonstration of a New Glycopeptidase, From Jack-Bean Meal, Acting on Aspartylglucosylamine Linkages" by Kota Sugiyama, et al., vol. 112, Nov. 1, 1983, Copyright 1983 by Academic Press, Inc., Biochemical and Biophysical Research Communications, pp. 155-160.

(Continued)

*Primary Examiner*—Walter D Griffin
*Assistant Examiner*—Shanta G Doe
(74) *Attorney, Agent, or Firm*—Dickstein Shapiro LLP

(57) ABSTRACT

The present invention provides a sugar chain purification instrument which can continuously and efficiently purify the sugar chain. According to the present invention, the instrument includes an immobilized protease column in which a carrier which can be packed in the column and on which protease is immobilized is packed and an immobilized glycopeptidase column in which a carrier which can be packed in the column and on which glycopeptidase is immobilized is packed, these columns being connected in series, and the reaction is carried out while continuously passing a glycoprotein to be decomposed together with a suitable buffer solution through the above columns. The step of liberation of sugar chain from the glycoprotein is highly simplified and labor-saving, and liberation of the sugar chain can be moderately and simply performed.

11 Claims, 2 Drawing Sheets

OTHER PUBLICATIONS

"Demonstration of Peptide:N-Glycosidase F Activity in Endo-β-N-acetylglucosaminidase F Preparations," Thomas Plummer, et al., vol. 259, No. 17, Issue of Sep. 10, pp. 10711-10704, 1984, The Journal of Biological Chemistry.

"A 500-MHz 1H-NMR Study on the N-Linked Carbohydrate Chain of Bromelain," J.A. Van Kuik, et al., Glycoconjugate J (1986) 3: 27-34.

Palm, Anders K. and Novotny, Milos V., "Analytical characterization of a facile porous polymer monolithic trypsin microreactor enabling peptide mass mapping using mass spectrometry". Rapid Commun. Mass Spectrum. (2004); 18:1374-1382.

Palm, Anders K. and Novotny, Milos V., "A monolithic PNGase F enzyme microreactor enabling glycan mass mapping of glycoproteins by mass spectrometry", Rapid Commun. Mass Spectrom. (2005); 19:1730-1738.

* cited by examiner

FIG. 1

| | THE PRESENT INVENTION | CONVENTIONAL METHOD | |
|---|---|---|---|
| ○ | A PURIFIED GLYCOPROTEIN SAMPLE IS DISSOLVED IN 125 mM TRIS - HYDROCHLORIC ACID BUFFER SOLUTION (ph8.6) CONTAINING 2 mM OF MERCAPTOETHANOL, 1% OF NONIDATE P - 40 AND 0.1% OF SDS. | A PURIFIED GLYCOPROTEIN SAMPLE IS DISSOLVED IN 200 mM TRIS - HYDROCHLORIC ACID BUFFER SOLUTION CONTAINING 10 mM OF CaCl$_2$ AND 0.05% OF NaN$_3$ TO PREPARE A REACTION SOLUTION. IT IS CONFIRMED THAT ph OF THE SOLUTION IS NEUTRAL. | ○ |
| × | | THE REACTION SOLUTION IS IMMERSED IN A BOILING WATER BATH OF 100°C AND HEATED FOR 10 MINUTES TO MODIFY THE PROTEIN. | ○ |
| × | | 0.1% M NaOH IS ADDED TO THE REACTION SOLUTION TO ADJUST THE ph TO 8.4. | ○ |
| ○ | THE REACTION SOLUTION IS INJECTED TO CARRY OUT REACTION IN COLUMN 4 - COLUMN 5 (37°C, 24 HOURS). | α - CHYMOTRYPSIN AND TRYPSIN ARE ADDED TO CARRY OUT DIGESTION (37°C, 24 HOURS). | ○ |
| × | | IT IS CONFIRMED THAT ph OF THE REACTION SOLUTION IS 8.4, AND FURTHER α - CHYMOTRYPSIN AND TRYPSIN ARE ADDED TO CARRY OUT DIGESTION (37°C, 24 HOURS). | ○ |
| × | | 0.1% M HCl IS ADDED TO THE REACTION SOLUTION TO ADJUST THE ph TO 5. | ○ |
| × | | THE REACTION SOLUTION IS IMMERSED IN A BOILING WATER BATH TO DEACTIVATE α - CHYMOTRYPSIN AND TRYPSIN (100°C, 10 MINUTES). | ○ |
| × | | THE REACTION SOLUTION IS DRIED UP UNDER REDUCED PRESSURE. | ○ |
| × | | THE RESIDUE IS DISSOLVED IN 125 mM TRIS - HYDROCHLORIC ACID BUFFER SOLUTION (ph8.6) CONTAINING 2 mM OF MERCAPTOETHANOL, 1% OF NONIDATE P - 40 AND 0.1% OF SDS. | ○ |
| △ | IF NECESSARY, THE BUFFER SOLUTION TO BE PASSED IS CHANGED. | IT IS CONFIRMED THAT THE REACTION SOLUTION HAS A ph OF ABOUT 8, AND N - GLYCANASE IS ADDED (37°C, 24 HOURS). | ○ |
| × | | THE REACTION SOLUTION IS DRIED UP UNDER REDUCED PRESSURE. | ○ |
| × | | THE RESIDUE IS DISSOLVED IN 200 mM TRIS - HYDROCHLORIC ACID BUFFER SOLUTION (ph8.4) CONTAINING 10 mM OF CaCl$_2$ AND 0.05% OF NaN$_3$. | ○ |
| △ | IF NECESSARY, FURTHER PASSING IS CARRIED OUT THROUGH THE IMMOBILIZED PROTEASE COLUMN. | ACTINASE IS ADDED AND THE REMAINING PEPTIDE FRAGMENT IS DECOMPOSED TO AMINO ACID (37°C, 24 HOURS). | ○ |
| ○ | THE EFFLUENT IS RECOVERED AND PURIFIED BY GEL FILTRATION TO OBTAIN SACCHARIDE CHAIN OF GLYCOPROTEIN AS A MIXTURE. | THE REACTION SOLUTION IS PURIFIED BY GEL FILTRATION TO OBTAIN SACCHARIDE CHAIN OF GLYCOPROTEIN AS A MIXTURE. | ○ |

○ : NECESSARY     × : UNNECESSARY     △ : IF NECESSARY

SACCHARIDE COMPOSITION PURIFICATION INSTRUMENT

INCORPORATION BY REFERENCE

The present application claims priority from Japanese application JP2004-101799 filed on Mar. 31, 2004, the content of which is hereby incorporated by reference into this application.

BACKGROUND OF THE INVENTION

The present invention relates to a sugar chain purification instrument for purification by separation of sugar chain from glycoprotein.

For analysis of sugar chain structure of glycoprotein, it is necessary to separate the sugar chain from glycoprotein. The separation is carried out either by liberating the sugar chain with enzyme or by chemically breaking glycosidic linkage.

As the enzymes which liberate asparagine-linked sugar chain, there are glycopeptidase derived from almonds (Biochem. Biophys. Res. Commun., 76, 1194), glycopeptidase derived from sword beans (Biochem. Biophys. Res. Commun., 112, 155), and N-glycanase (J. Biol. Chem., 259, 10700). Furthermore, as a method for carrying out chemical breakage between sugar-protein, hydrazinolysis is mostly utilized, and other methods for chemical breakage of sugar chain include trifluoroacetolysis and use of $LiBH_4$.

When comparison is made on merits and demerits of the enzyme method and chemical method for breakage of sugar chain of glycoprotein, the merit of the enzyme method is that the operation of this method is considerably simpler than the hydrazinolysis. That is, the enzyme method does not require complete drying of samples and requires only leaving the sample overnight with addition of enzyme. Post-treatment of the reaction mixture is also simple, and the sugar portion is fractionated by carrying out a gel filtration using a suitable column. Another merit of the enzyme method is that no modification occurs on the broken sugar chains.

In the hydrazinolysis, acetyl group of N-acetylhexosamine is eliminated, and hence hexosamine must be again N-acetylated. Furthermore, in glycoprotein derived from vegetables, fucose is linked through α-1,3 linkage to N-acetylglucosamine linking to aspargine, and it is reported that this fucose is readily liberated especially under the conditions of hydrazinolysis (Glycoconjyugate J., 3, 27).

Furthermore, when an enzyme is allowed to directly act on glycoprotein, sugar chain of the glycoprotein may not completely be liberated due to the steric hindrance caused by the higher order structure of protein, and, on the other hand, in the hydrazinolysis, the protein to which the sugar chain links is decomposed to amino acid, and hence the hydrazinolysis is not effective to presume the higher order structure of glycoprotein. It is known that the glycopeptidase derived from almonds which is most frequently used at present acts on any sugar chains without discrimination of structure among aspargine-linked sugar chains which are asialated, and furthermore an especially high reaction efficiency is exhibited in case the glycoprotein is decomposed to glycopeptide molecules which are made smaller to some extent by peptidase treatment or the like. However, the hydrazinolysis is superior in that aspargine-linked sugar chain can be cut out irrespective of presence or absence of sialic acid in the sugar chain or irrespective of the higher order structure of protein.

From the above, it can be considered that purification of sugar chain of glycoprotein by two-stage enzyme reactions which include digestion of protein portion with peptidase as a former stage before reaction with glycopeptidase which can perform moderate and simple liberation of sugar chain is very effective for analysis of structure of sugar chain of glycoprotein. With progress of microbiology and biochemistry, biocatalysts such as microorganisms and enzymes are utilized widely and industrially, but in many cases, the process is batch-wise, which comprises introducing a biocatalyst into a substrate solution and removing the biocatalyst after completion of reaction.

One example of conventional process is shown in the right column of the table shown in FIG. 1.

According to the conventionally employed batch process, a large reaction vessel must be used for every batch and hence a large plant is required. Furthermore, since it is very difficult to recover and reuse the biocatalyst which has been once used, the biocatalyst which has been used for one reaction is abandoned. Enzymes are originally extracted from organisms, and are expensive even in a small amount. Therefore, the conventional processes which abandon the enzymes used for one reaction are considerably uneconomical.

The object of the present invention is to provide a sugar chain purification instrument which can continuously and efficiently carry out purification of sugar chain.

SUMMARY OF THE INVENTION

For attaining the above object, according to the present invention, a first column in which an enzyme for decomposing glycoprotein to glycopeptide is immobilized is connected with a second column in which an enzyme for decomposing glycopeptide to sugar chain and peptide is immobilized, and a sample is introduced into these columns to liberate sugar chain.

Specifically, the first column is an immobilized protease column and the second column is an immobilized glycopeptidase column.

By using the sugar chain purification instrument of the present invention, the step for liberation of sugar chain of glycoprotein which has been very troublesome is markedly simplified and saved troubles, and the sugar chain can be moderately and simply liberated.

Moreover, there can be constructed a system for automatic purification of sugar chain of glycoprotein which is high in throughput. Moreover, according to this system, recovery can be improved because it is a closed system for the whole steps.

Other objects, features and advantages of the invention will become apparent from the following description of the embodiments of the invention taken in conjunction with the accompanying drawings.

BRIEF DESCRIPTION OF DRAWINGS

FIG. 1 compares the present invention and conventional process on purification of sugar chain of glycoprotein.

Figure 2:
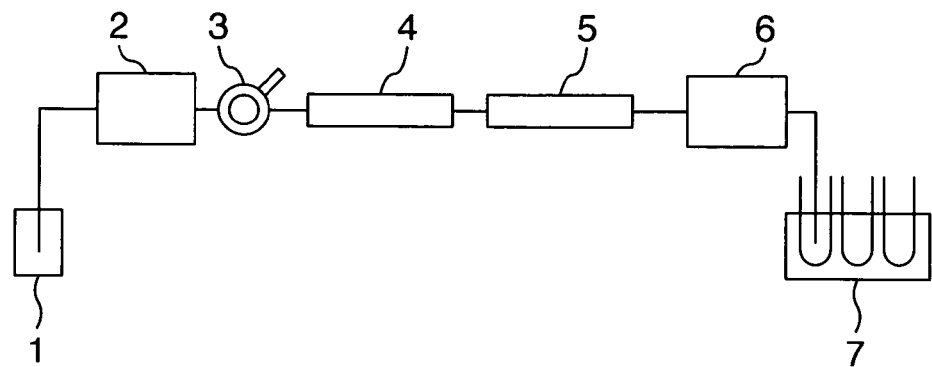
FIG. 2 is a diagrammatic view of the sugar chain purification instrument of Example 1.

In the drawings, the reference numerals indicate the followings. 1—buffer solution, 2—pump, 3—injector, 4, 23—immobilized protease columns, 5, 24—immobilized glycopeptidase columns, 6—detector, 7—fraction collector, 8—washing fluid, 9—selector valve a, 10—selector valve b, 11—selector valve c, 12—connection flow path a, 13—connection flow path b, 14—selector valve d, 15—selector valve e, 16—selector valve f, 17—detector, 18—connection flow path c, 19—connection flow path d, 20—selector valve g, 21—selector valve h, 22—drain

DETAILED DESCRIPTION OF THE INVENTION

The present invention resides in providing a column in which an enzyme is immobilized depending on the step for liberation of sugar chain in order to use the enzyme not only once, but repeatedly.

For the purpose of using an enzyme not only once, but also repeatedly, the enzyme is used as an immobilized enzyme which is attached to glass beads, cellulose, plastic film, active carbon, silica gel, or the like. If the enzyme is firmly immobilized by chemical bonding or the like, this serves as a reaction substrate, and when a sample is passed therethrough, the enzyme reacts well with the sample and furthermore escaping of the enzyme can be inhibited. When this stabilized immobilized enzyme is packed in a column and used as a reactor, the enzyme can be used a plurality of times, and the reaction efficiency is improved.

It is generally said that recovery, reuse, enhancement of stability and application into organic solvents of enzymes become possible by immobilization of the enzymes. However, since microscopic changes of environment around the enzyme molecules caused by immobilization greatly affect function and stability of the enzyme, it is necessary to select immobilization carriers having proper physical and chemical characteristics depending on the use and investigate the immobilization method depending on the enzyme after trying various immobilization methods.

Merits of general immobilized enzymes are as follows.
(1) The initiation and termination of the reaction can be easily controlled by the addition and removal of the immobilized enzyme.
(2) The separation of enzyme and product from each other is easy and the process can be simplified.
(3) Since the reaction can be allowed to proceed by passing a raw material solution through a column packed with the immobilized enzyme, the apparatus can be made smaller.
(4) The enzyme can be used repeatedly and the process is economical.
(5) Stability of enzymes or microorganisms is improved by the immobilization (in some case).

Various methods for immobilization of enzyme on the surface of a solid have been developed, and they can be roughly classified into the following three methods.
(1) Carrier binding method: A method of binding the enzyme to a water-insoluble carrier.
(2) Crosslinking method: A method of subjecting the enzyme to crosslinking reaction with a reagent having 2 or more functional groups to insolubilize the enzyme without using carrier.
(3) Entrapping method: A method of wrapping the enzyme in minute lattice of gel or covering the enzyme with a semitransparent polymer film.

There are many reports that stability of enzyme is generally improved by immobilization, and the reason is considered as follows.

Enzyme (protein) has a complicated higher order structure, and its stereostructure greatly acts on the catalytic ability or substance identification ability of enzyme. When the stereostructure is broken by heat or chemicals, the enzyme is modified to lose catalytic ability. It is considered that in the case of enzyme being immobilized, a plurality of chemical linkages are produced between enzyme-carrier, whereby the stereostructure of enzyme is generally reinforced and enzyme becomes difficult to modify. When enzyme is industrially used, the enzyme is required to act stably over a long period of time, and hence it is preferred to improve stability of enzyme by immobilization.

A suitable amount of protease is immobilized through covalent bond on an immobilization carrier which is swollen well in an aqueous solvent to obtain immobilized protease, and this immobilized protease is packed in a column to obtain an immobilized protease column. Furthermore, glycopeptidase is immobilized through covalent bond to obtain immobilized glycopeptidase, and this is packed in a column to obtain an immobilized glycopeptidase.

As mentioned above, two columns different in action are obtained. The immobilized protease column is set at the former stage and the immobilized glycopeptidase column is set at the latter stage in succession. When a glycoprotein solution previously modified with heat is passed through these continuous columns, partial decomposition of the glycoprotein takes place firstly in the immobilized protease column to produce glycopeptide. When this glycopeptide solution is successively passed through the immobilized glycopeptidase column, sugar chain of glycoprotein is liberated in the form of aspartic acid being linked to the reduction end side of the sugar chain. The number of passing of the solution through the respective columns and the number of the immobilized enzyme columns used are adjusted as desired. The finally produced sugar chain is taken out by a fraction collector, whereby sugar chain can be separated from the glycoprotein and purified.

The carriers which can be used and packed in columns in the present invention are not particularly limited, and include, for example, cellulose, carriers originating from polysaccharides such as agarose, chitin and chitosan, or derivatives thereof, acrylamide derivatives, methacrylamide derivatives, polymers of acrylic acid or methacrylic acid, polystyrene derivatives, copolymers of them with other vinyl compounds, carriers originating from polyvinyl compounds such as polyvinyl alcohol, polyethylene glycol and polypropylene glycol, silica gel derivatives or mixtures thereof, and beads of magnetic materials originating from metal oxides.

There are no limitation in linkers in the present invention in which the molecular structure reacting with selective functional groups can form covalent bond by causing chemical reaction or photoreaction in an aqueous solvent under moderate conditions or which contain a structure having affinity bonding ability, ionic bonding ability or hydrophobic bonding ability for protease, glycoprotein and glycopeptidase, but from the viewpoint of causing no leakage of enzymes, preferred are linkers which can immobilize enzymes through covalent bonds, such as photofunctional groups, e.g., amino group, carboxyl group, active esters of carboxylic acid, epoxy group, aldehyde group, imidazole group, hydroxyl group, CNBr group, thiol group, SAND, ANB-NOS and SANPAH.

For example, unspecific amino group on the surface of enzyme protein easily forms amide bond with beads such as of agarose having 6-aminohexanoic acid N-hydroxysuccinimide ester in a buffer solution having a pH of 5-10, and, as a result, the protein is immobilized. Since such a carrier is commercially available, the immobilized enzyme can be very easily prepared. Furthermore, there is a report that immobilization of protein terminates in about 3 hours for carriers having ligands relatively readily becoming unstable in water, such as CNBr agarose, and therefore various combinations of immobilization carriers and ligands and enzymes can be investigated. The selection of the combination is also not particularly limited, and it suffices that enzyme used is stable at a pH suitable for the reaction of ligand. Moreover, length of the ligand may also be selected considering the size of protein to be immobilized.

The proteases used in the present invention are also not particularly limited. Proteases are classified into various groups according to their substrate specificity, but since the glycoprotein which is a raw material from which sugar chain is separated is also a molecule of high diversity as mentioned above, it is necessary to select enzymes according to the glycoprotein from which sugar chain is to be separated. Generally, trypsin, chymotrypsin, thermolysin and pepsin are often used. However, when subsequent sugar chain liberation reaction is carried out with glycopeptidase, the efficiency of liberation of sugar chain may greatly change depending on the structure of glycopeptide which is a substrate, and therefore it is necessary that various immobilized enzyme columns are prepared and are used depending on the structure of sugar chain to be separated. For example, it is said that the number of amino acids in the peptide site of the substrate glycopeptide is suitably 3-30. However, it is known that as a result of being decomposed by the protease treatment of the former stage, in the case of the amino acid linked to the sugar chain being one aspargine, the releasing efficiency of sugar chain with glycopeptidase is very low. Therefore, when decomposition with protease prior to the glycopeptidase treatment is carried out, it is necessary to carefully select the enzymes. In case there is the possibility of sialic acid being linked to the sugar chain liberated, in order to obtain the sugar chain together with sialic acid, protein is once subjected to reductive carboxymethylation and thereafter thermolysin is used under neutral conditions. When sialic acid may be broken, digestion with pepsin is carried out under acidic conditions.

The glycoprotein and glycopeptidase in the present invention mean endoglycosidase and the kinds thereof are not particularly limited, and preferred are endoglycosidase D, endoglycosidase H, endoglycosidase F, peptide-N-glycosidase F, endo-α-N-acetylgalactosaminidase, and endo-β-galactosidase.

DESCRIPTION OF PREFERRED EMBODIMENTS

The present invention will be explained in more detail below.

Example 1

FIG. 2 shows a diagrammatic view of the sugar chain purification instrument of the present invention. A buffer solution 1 is fed by a pump 2 and a sample containing glycoprotein is injected into the flow of buffer solution 1 by an injector 3. The sample passes through an immobilized protease column 4 and an immobilized glycopeptidase column 5 to liberate sugar chain. The liberated sugar chain is detected by a detector 6 and is collected by a fraction collector 7. As the detector 6, for example, a UV detector which detects ultraviolet absorption is used.

The immobilized protease column 4 and the immobilized glycopeptidase column 5 will be explained in detail below.

The immobilized protease column 4 was produced in the following manner.

0.5 g of CNBr activated agarose gel was washed separately three times with 100 mL of 1 mM hydrochloric acid. Thereto was added 5 mL of 200 mM tris-hydrochloric acid buffer solution (pH 8.2) containing 1000 units of trypsin derived from pig pancreas, 10 mM of $CaCl_2$ and 0.05% of $NaN_3$, followed by gently shaking the mixture at 4° C. for 12 hours. The immobilized enzyme was filtered off by a glass filter, and is washed with 5 mL of the above buffer solution containing no trypsin. In the above buffer solution was dissolved bovine serum albumin so as to give a concentration of 2 mg/mL, and then the immobilized enzyme was washed with the above buffer solution to block the unreacted active groups. The immobilized enzyme was washed with 1 M aqueous sodium chloride solution and then with distilled water, and thereafter the immobilized enzyme was immersed in a 50 mM tris-hydrochloric acid buffer solution (pH 8.2) containing 10 mM of $CaCl_2$ and 0.05% of $NaN_3$ and stored at 4° C. This immobilized trypsin derived from pig pancreas was packed in a column to obtain the immobilized protease column 4.

The immobilized glycopeptidase column 5 was produced in the following manner.

50 mg of N-succinimidyl-6-[4'-azido-2'-nitrophenylamino] hexanoate was dissolved in 2.56 mL of dimethyl sulfoxide. 2.7 mL of hydrophilic vinyl polymer beads modified with amino group was suspended in 23.0 mL of a 100 mM sodium phosphate buffer solution (pH 7.2) containing 50 mM of EDTA 2Na and 0.05% of sodium azide, and to the suspension was added N-succinimidyl-6-[4'-azido-2'-nitrophenylamino] hexanoate solution, followed by shaking at room temperature for 24 hours while shielding the light. While the beads to which N-succinimidyl-6-[4'-azido-2'-nitrophenylamino] hexanoate was bound was filtered off by a glass filter under shielding the light, the beads were washed with 300 mL of a 20 mM phosphoric acid buffer solution (pH 7.2) containing 10% (v/v) of dimenthyl sulfoxide (DMSO) separately several times under shielding the light. Subsequently, the beads were also washed with 300 ml of a 20 mM sodium phosphate buffer solution (pH 7.2) containing 10 mM of EDTA·2Na and 0.05% of sodium azide, and transferred into a container of 15 mL to obtain a carrier for immobilization of glycopeptidase derived from Flavobacterium maningoseoticum. To 2.7 mL of this immobilization carrier was added 4.0 mL of a 20 mM sodium phosphate buffer solution (pH 7.2) containing 10 mM of EDTA·2Na and 0.05% of sodium azide, and then thereto was added 50 milliunits of glycopeptidase derived from Flavobacterium maningoseoticum dissolved in 1.0 mL of this sodium phosphate buffer solution, followed by irradiating with ultraviolet rays of 300 nm under shaking while shielding the light to carry out the reaction at room temperature for 12 hours. Then, centrifugal separation was carried out at 8400 g and the beads were recovered, and then the beads were washed with 100 mL of the buffer solution used for the reaction to obtain immobilized glycopeptidase. This was packed in a column to obtain the immobilized glycopeptidase column 5.

An example of carrying out a reaction of liberation of sugar chain by the instrument in which are incorporated the resulting immobilized protease column 4 and immobilized glycopeptidase column 5 connected as shown in FIG. 2 is shown in the left column of the table shown in FIG. 1.

100 mg of purified egg albumin was dissolved in 1 mL of a 125 mM tris-hydrochloric acid buffer solution (pH 8.6) containing 2 mM of mercaptoethanol, 1% of Nonidate P-40 and 0.1% of SDS, and this solution was injected as a sample from injector 3. Pump 2 passed the buffer solution 1 at a flow rate of 2 μL/min. The injected sample was allowed to flow into the immobilized glycopeptidase column 5 through the immobilized protease column 4 to carry out the reaction. The column temperature was 37° C. and the reaction time was 24 hours. The reaction solution discharged from the immobilized glycopeptidase column 5 was subjected to measurement of ultraviolet absorption by the detector 6, and the fraction having ultraviolet absorption was collected by the fraction collector 7. In the reaction solution discharged from the immobilized glycopeptidase 5, sugar chain was liberated from peptide, and hence only the sugar chain could be taken out.

Furthermore, as can be seen from FIG. 1, by using the instrument of this example, purification of sugar chain can be performed by a method very simpler than conventional methods.

For example, the heat treating step for deactivation of protease after digestion of protein which is essential in the conventional methods is not necessary in this instrument, and the problem that the glycoprotease to be used for the subsequent reaction is decomposed with the remaining protease in the former step can be easily solved by using the instrument of this example. Therefore, this purification instrument is simplified and saved the trouble in such an extent that when a glycoprotein sample is once injected into this system, only the liberated sugar chain and amino acid are obtained, and thus the operation steps can be automated.

Example 2

In Example 1, purification of sugar chain was carried out with connecting one immobilized protease column 4 and one immobilized glycopeptidase column 5, but for some kind of the glycoprotein, the purification cannot sometimes be performed by using one kind of protease or one kind of glycopeptidase. In this case, the purification must be carried out using a plurality of immobilized protease columns and a plurality of immobilized glycopeptidase columns. This example will be explained using FIG. 3.

Figure 3:
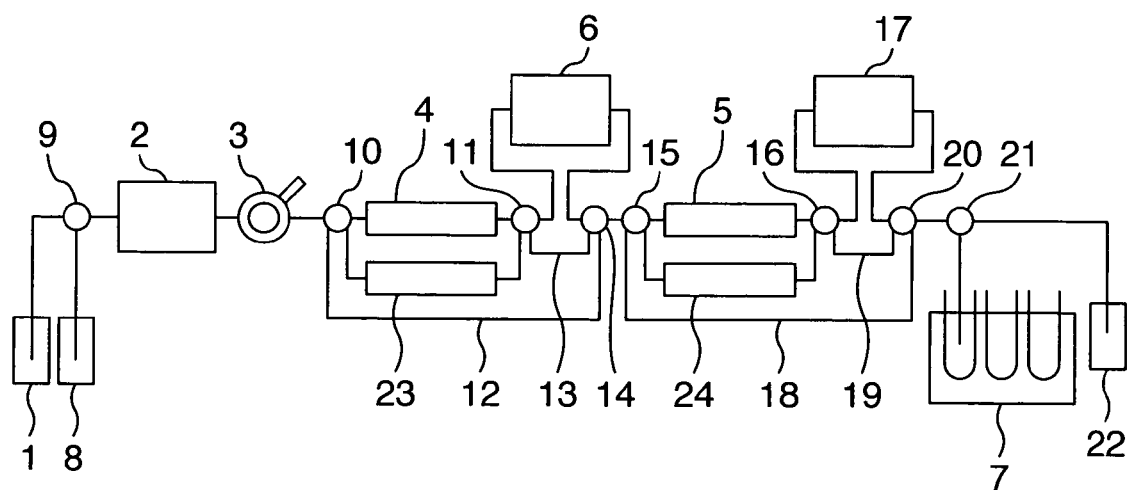
FIG. 3 is a diagrammatic view of the sugar chain purification instrument of Example 2.

FIG. 3 shows an example where the sugar chain purification instrument was constructed using two kinds of immobilized protease columns and two kinds of immobilized glycopeptidase columns.

Here, the selector valve b 10 can perform alternate switching between the flow path which connects the injector 3 and the immobilized protease column 4 or the immobilized protease column 23 and the flow path which connects the connection flow path a 12 and the immobilized protease column 23 or the immobilized protease column 4. The selector valve c 11 can perform alternate switching between the flow path which connects the immobilized protease column 4 and the connection flow path b 13 or the detector 6 and the flow path which connects the immobilized protease column 23 and the detector 6 or the connection flow path b 13. The selector valve d 14 can perform alternate switching between the flow path which connects the detector 6 and the selector valve e 15 or the connection flow path a 12 and the flow path which connects the connection flow path b 13 and the connection flow path a 12 or the selector valve e 15.

The selector valve e 15 can perform alternate switching between the flow path which connects the selector valve d 14 and the immobilized glycopeptidase column 5 or the immobilized glycopeptidase column 24 and the flow path which connects the connection flow path c 18 and the immobilized glycopeptidase column 24 or the immobilized glycopeptidase column 5. The selector valve f 16 can perform alternate switching between the flow path which connects the immobilized glycopeptidase column 5 and the connection flow path d 19 or the detector 17 and the flow path which connects the immobilized glycopeptidase column 24 and the detector 17 or the connection flow path d 19. The selector valve g 20 can perform alternate switching between the flow path which connects the detector 17 and the selector valve h 21 or the connection flow path c 18 and the flow path which connects the connection flow path d 19 and the connection flow path c 18 or the selector valve h 21.

In the instrument of FIG. 3, the treatment is carried out, for example, in the following manner.

The pump 2 feeds the buffer solution 1, and a sample is injected from the injector 3. The injected sample is led to the immobilized protease column 4 through the selector valve b 10. Thereafter, the sample is led to the immobilized protease column 23 through the selector valve c 11, the connection flow path b 13, the selector valve d 14, the connection flow path a 12 and the selector valve b 10. Thus, the glycoprotein can be divided to glycopeptide by the two columns. The glycopeptide is introduced into a step conducted by the next immobilized glycopeptidase column through the selector valve c 11, the detector 6 and the selector valve d 14.

The solution led from the selector valve d 14 is led to the immobilized glycopeptidase column 5 through the selector valve e 15. Thereafter, it is led to the immobilized glycopeptidase column 24 through the selector valve f 16, the connection flow path d 19, the selector valve g 20, the connection flow path c 18 and the selector valve e 15. Thus, the sugar chain can be liberated from peptide by the two kinds of the immobilized glycopeptidase columns. Thereafter, the sugar chain is led to the side of fraction collector 7 through the selector valve f 16, the detector 17 and the selector valve g 20.

In collecting the sugar chain by the fraction collector 7, the selector valve h 21 is switched to the side of the fraction collector 7, the ultraviolet absorption is measured by the detector 17, and fractions having ultraviolet absorption are collected by the fraction collector 7.

In the above treatment, the sample is passed once through the two immobilized protease columns and the two immobilized glycopeptidase columns, and the treatment is not limited to this procedure and the sample may be passed a plurality of times through the respective columns. This can be easily carried out by control of the respective selector valves. Furthermore, the respective immobilized protease columns and the immobilized glycopeptidase columns may be different or the same in properties.

Moreover, in the example of FIG. 3, a means for washing is provided.

In carrying out the washing, the selector valve a 9 is switched to the side of washing fluid 8, the selector valve b 10 is switched to the side of the immobilized protease column 4, the selector valve c 11 is switched to the side where the immobilized protease column 4 and the connection flow path b 13 are connected, the selector valve d 14 is switched to the side where the connection flow path b 13 and the selector valve e 15 are connected, the selector valve e 15 is switched to the side where the selector valve d 14 and the connection flow path c 18 are connected, the selector valve g 20 is switched to the side where the connection flow path c 18 and the selector valve h 21 are connected, and the selector valve h 21 is switched to the side of drain 22, and thereafter the washing fluid 8 is passed by the pump 8 to carry out washing of the immobilized protease column 4. By similarly switching the respective selector valves, washing of the immobilized protease column 23, the immobilized glycopeptidase column 5 and the immobilized glycopeptidase 24 can be performed.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A sugar chain purification instrument for separating sugar chain from a sample containing a glycoprotein which is provided with a pump for feeding a buffer solution, an injector for injecting the sample into the flow of the buffer solution, a first column in which an enzyme for decomposing glycoprotein to glycopeptide is immobilized, and a second column in which an enzyme for decomposing glycopeptide to peptide is immobilized, the sugar chain being obtained by collecting an effluent from the second column.

2. A sugar chain purification instrument according to claim 1, wherein a carrier which can be packed in the column and to which an enzyme for decomposing protein is bound is packed in the first column.

3. A sugar chain purification instrument according to claim 1, wherein a carrier which can be packed in the column and to which an enzyme for separating sugar chain from protein or peptide is bound is packed in the second column.

4. A sugar chain purification instrument according to claim 1 which is provided with a detector for detecting the solution discharged from the second column and a fraction collector collecting each of the components based on the results of detection by the detector.

5. A sugar chain purification instrument according to claim 1, wherein a plurality of the first columns are provided and a plurality of the second columns are provided, and furthermore a means for circulation between the plurality of the first columns and a means for circulation between the plurality of the second columns are provided.

6. A sugar chain purification instrument according to claim 5 which is provided with a first detector for detecting the solution discharged from the first column, a second detector for detecting the solution discharged from the second column, and a fraction collector collecting each of the components based on the results of detection by the second detector.

7. A sugar chain purification instrument according to claim 2, wherein the carrier which can be packed in the first and second columns is a carrier derived from polysaccharides, a carrier derived from polyvinyl compounds, a silica gel derivative, beads of magnetic material derived from metal oxides, a copolymer or a mixture thereof.

8. A sugar chain purification instrument according to claim 3, wherein the carrier which can be packed in the first and second columns is a carrier derived from polysaccharides, a carrier derived from polyvinyl compounds, a silica gel derivative, beads of magnetic material derived from metal oxides, a copolymer or a mixture thereof.

9. A sugar chain purification instrument according to claim 2, wherein the enzyme is protease, peptidase, trypsin, chymotrypsin, thermolysin or pepsin.

10. A sugar chain purification instrument according to claim 3, wherein the enzyme is endoglycosidase, endoglycosidase D, endoglycosidase H, endoglycosidase F, peptide-N-glycosidase F, endo-α-N-acetylgalactosaminidase or endo-β-galactosidase.

11. A sugar chain purification instrument according to claim 1, wherein the pump feeds a washing fluid, which washes the first and second columns.

* * * * *